Figure 1:
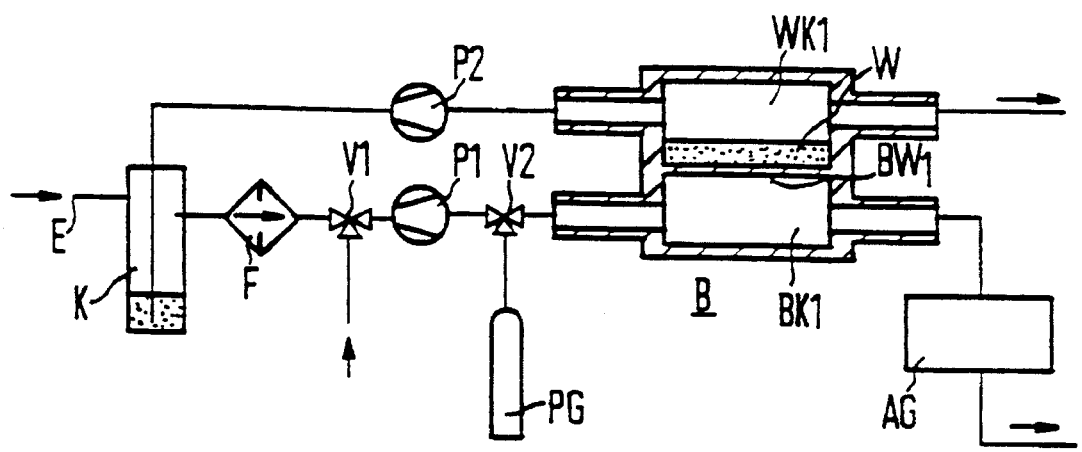

United States Patent [19]
Kimmig

[11] Patent Number: 5,563,330
[45] Date of Patent: Oct. 8, 1996

[54] METHOD AND DEVICE FOR MEASURING THE CONCENTRATION OF A DETECTOR GAS IN A MEASURING GAS CONTAINING AN INTERFERING GAS

[75] Inventor: Ludwig Kimmig, Ettlingen, Germany

[73] Assignee: Siemens Aktiengesellschaft, München, Germany

[21] Appl. No.: 325,226

[22] PCT Filed: Apr. 13, 1993

[86] PCT No.: PCT/DE93/00333

§ 371 Date: Oct. 21, 1994

§ 102(e) Date: Oct. 21, 1994

[87] PCT Pub. No.: WO93/21515

PCT Pub. Date: Oct. 28, 1993

[30] Foreign Application Priority Data

Apr. 21, 1992 [DE] Germany .................. 42 13 051.4

[51] Int. Cl.⁶ .................................................. G01N 21/35
[52] U.S. Cl. ...................... 73/23.21; 73/31.07; 73/23.31; 55/270; 261/104
[58] Field of Search .................... 73/23.31, 23.21, 73/31.07; 55/257.7, 267, 270; 95/288; 261/104, 107; 422/168, 169

[56] References Cited

U.S. PATENT DOCUMENTS

| | | | |
|---|---|---|---|
| 3,532,270 | 10/1970 | Schoen, Jr. | 261/104 |
| 3,572,994 | 3/1971 | Hochstrasser | 261/104 |
| 4,160,373 | 7/1979 | Fastaia et al. | 73/23.31 |
| 4,517,135 | 5/1985 | Szerenyi et al. | 261/104 |
| 4,555,931 | 12/1985 | Amimoto et al. | 73/23.31 |
| 4,953,390 | 9/1990 | Krempl et al. | 250/343 |
| 5,297,432 | 3/1994 | Traina et al. | 73/23.31 |

FOREIGN PATENT DOCUMENTS

| | | | |
|---|---|---|---|
| 0343143 | 11/1989 | European Pat. Off. | |
| 4021864 | 1/1991 | Germany . | |
| 221646 | 9/1989 | Japan | 73/31.07 |
| 514555 | 11/1939 | United Kingdom | 261/104 |
| 03029 | 4/1989 | WIPO . | |

OTHER PUBLICATIONS

Patent Abstracts of Japan, vol. 9, No. 62 19 Mar. 1985 & JP-A-59 196 461 (Shimazu Seisakusho) 7 Nov. 1984.
Book *Messen, Steuern und Regeln in der Chemischen Technik*, 3rd ed., vol. II, p. 611, J. Hengstenberg et al.

Primary Examiner—Hezron E. Williams
Assistant Examiner—Daniel S. Larkin
Attorney, Agent, or Firm—Kenyon & Kenyon

[57] ABSTRACT

A concentration of a detector gas in a measuring gas containing an interfering gas is measured. A zero gas that is free of the detector gas and/or a test gas having a known concentration of the detector gas are supplied to an analyzer such as a non-dispersive infrared (NDIR) gas analyzer. Interfering gas is added to the measuring gas, the zero gas, and in some instances, to the test gas to an extent which allows the interfering gas to have a same concentration in each case.

27 Claims, 1 Drawing Sheet

METHOD AND DEVICE FOR MEASURING THE CONCENTRATION OF A DETECTOR GAS IN A MEASURING GAS CONTAINING AN INTERFERING GAS

In non-dispersive infrared (NDIR) gas analysis, the problem of cross sensitivity arises when the measuring gas not only contains the detector gas, whose concentration in the measuring gas is supposed to be measured, but also contains an interfering gas, whose spectral absorbance bands substantially overlap those of the detector gas. This happens, for instance, when nitrogen oxides are measured in exhaust gases, which contain water vapor as an interfering gas. To remove water vapor and other interfering gases as well, the book *Messen, Steuern und Regeln in der chemischen Technik* [Measuring, Controlling and Adjusting in Chemical Technology], 3rd edition, volume II, p. 611, Springer publishing house, 1980, discloses cooling the measuring gas and subsequently directing it over a drying agent that has to be renewed from time to time.

To measure nitrogen oxides in the exhaust gas of motor vehicle engines, the International Patent Application WO 89/03029 also discloses cooling the measuring gas in order to remove the water vapor contained in the gas and, in this manner, to facilitate the nitrogen oxide measurement. The disadvantage of the known measures for removing water vapor is that an expensive cooler is needed, which is subjected to wear, and that operating and maintenance costs accrue.

The underlying object of this invention is to indicate a method and a device for measuring the concentration of a detector gas in a measuring gas containing an interfering gas, which is simpler than known methods and will ensure better operational reliability.

The idea behind the invention is to add so much interfering gas to the measuring gas, the zero gas, and the test gas that the same interfering gas concentration will be reached in each case. When the original concentration of interfering gas in the measuring gas is more or less the same or is higher, it can be necessary to lower the concentration by means of cooling. For this purpose, it generally suffices to simply cool the measuring gas to about the ambient temperature. It is beneficial to more or less retain the original concentration of the interfering gas or to only change it slightly, because any such change also affects the concentration of the detector gas, and this generally has to be allowed for in a corrective calculation.

The measured value determined with the zero gas corresponds to a zero concentration of the detector gas and, therefore, constitutes the zero point. This value is subtracted from the measured values of the measuring gas and, in fact, either arithmetically or, in the case of double-beam NDIR analyzers, physically. When the test gas, which contains the detector gas in a known concentration, is measured, the increase in the measuring effect is determined.

In the case that the concentration of nitrogen oxides in water-vapor-containing exhaust gas is measured using a single-beam NDIR analyzer, the measuring, zero, and test gases are directed one after another through a single humidifier. This has the advantage that the gases are moistened in the same manner. However, a measuring pause must be observed from time to time to redefine the zero point and the increase. This generally does not interfere, since when measuring exhaust gases from motor vehicle engines, for example, the measuring pauses that are required anyway can be utilized. In the case of a double-beam analyzer, the zero gas can be used as a reference gas, so that the zero point does not need to be determined separately. In this case, however, two humidifiers are needed, preferably with a combined construction, so that largely conforming conditions, for example the same temperatures, will prevail for the moistening operation.

In one advantageous specific embodiment, the humidifier contains a humidifying chamber, through which the gases are directed and which has a moistening wall made of a material, which absorbs the water and releases it to gases that are not saturated with water vapor. In one specific embodiment, which is especially simple, but is less suited for a higher measuring accuracy, the moistening wall removes water vapor from the measuring gas and releases it again to the zero gas and the test gas. In this manner, one compensates for the originally variable water-vapor content of the gases, for example of the exhaust gas, ambient air and test gas from a bottle. The moistening wall is preferably brought into contact on its rear side with water in liquid or vaporous form, which it absorbs and releases to the gas flowing through the moistening chamber.

On the basis of the drawing, the invention, as well as further advantages, developments and additions are described in greater detail and clarified in the following.

FIG. 1 schematically depicts an arrangement for measuring the concentration of nitrogen oxides in exhaust gases.

Figure 2:
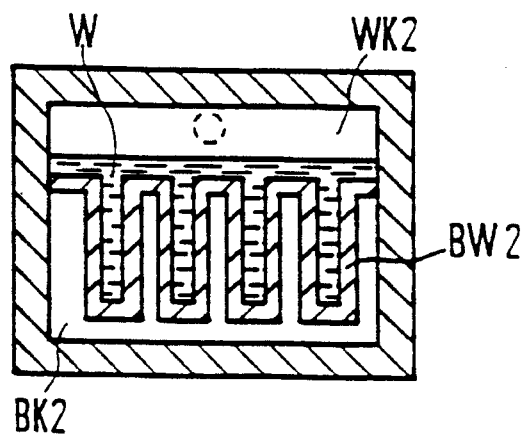

FIG. 2 shows a gas humidifier in cross-section, which can be used alternatively in the arrangement according to FIG. 1.

Exhaust gas from a motor vehicle engine is supplied to the arrangement shown in FIG. 1 via an inlet (entry site) E. The exhaust gas cools off in the line and arrives in a condensation separator (settling) tank K, at whose base the condensate water collects. The exhaust gas liberated from the excess water vapor flows through a filter F and through a valve V1 to a pump P1, which delivers the exhaust gas through a valve V2 into a moistening chamber BK1 of a humidifier B. From there, the gas arrives in an NDIR analyzer, which is used to measure the nitrogen-oxide concentration of the exhaust gas.

Situated above the moistening chamber BK1 in the humidifier B is a water-supply chamber WK1, into which a pump P2 pumps condensate water out of the condensation separator (settling) tank K, which collects there over a moistening wall BW1. This consists of a material, which absorbs water and releases it again, provided that it is circumflowed by gas that is not saturated with water vapor. In the exemplary embodiment, polyamide is used as such a material, which is reinforced with glass fiber to increase strength. The wall should be very thin, preferably a foil with a thickness of less than 1mm. Of course, the remaining parts of the humidifier B can also consist of this material. Also, the humidifier can be constructed so as to allow water to flow completely around a moistening chamber.

The measuring gas flowing through the moistening chamber BK1 absorbs water vapor from the moistening wall BW1 up to a specific concentration essentially given by the ambient temperature. Of course, the residence time in the moistening chamber BK1 must be long enough. Thus, interfering gas is added selectively to the measuring gas.

To compensate for the measuring effect caused by the interfering gas in the analyzer AG, the valve V1 is switched over during a measuring pause and ambient air is delivered by the pump P1 through the moistening chamber BK1 to the analyzer AG. This air absorbs moisture, as does the measuring gas.

Since it is essentially free of nitrogen oxide, it is solely the absorbed water vapor that determines the measuring effect. Therefore, if one subtracts the measured value determined in this case from the measured values acquired during the measurement of the exhaust gas, as a difference, one obtains a value, which corresponds to the concentration of the nitrogen oxide.

A vessel PG contains test gas, which in the present case is nitrogen oxide in a known concentration. With its help, a second point of the measuring characteristic of the measuring arrangement can be determined, in that the valve V2 is switched over and the test gas is supplied through the moistening chamber BK1 to the analyzer AG. Also, the test gas absorbs moisture in this case and, in fact, in the same concentration as the measuring gas and the zero gas. While the measured value of the zero gas yields the zero point of the measuring characteristic, the increase in the measuring effect is determined from the measured-value test gases.

To allow the gases flowing through the moistening chamber BK1 to absorb sufficient moisture, it might be necessary to increase the surface area of the moistening wall BW1, for instance, by roughening it. FIG. 2 shows another specific embodiment, where the moistening wall has a large surface area, in which a cross-section through a humidifier is shown. Its moistening wall BW2 has a meander-shaped design. It divides the humidifier into a moistening chamber BK2 and a water-supply chamber WK2. There is water W on the side of the water-supply chamber WK2 in the slits formed by the meander shape; the gas to be moistened flows through the meander-shaped slits inside the moistening chamber BK2. In place of the meander shape, any other form that enlarges the surface area can also be selected.

What is claimed is:

1. A method for measuring a concentration of a detector gas in a measuring gas containing an interfering gas, comprising steps of:

supplying at least one of a zero gas that is free of the detector gas and a test gas having a known concentration of the detector gas to an analyzer; and adding interfering gas to the measuring gas and to the zero gas to an extent such that a concentration of the interfering gas in the measuring gas is equal to a concentration of the interferinggas in the zero gas.

2. The method according to claim 1, further comprising steps of:

partially removing interfering gas from the measuring gas; and adding interfering gas to the partially removed measuring gas.

3. The method according to claim 1, wherein the interfering gas is water vapor, and further comprising a step of humidifying or moistening the measuring gas, the zero gas, and the test gas.

4. The method according to claim 1, wherein said adding step adds interfering gas to the test gas.

5. The method according to claim 4, further comprising steps of:

partially removing interfering gas from the measuring gas; and adding interfering gas to the partially removed measuring gas.

6. The method according to claim 4, wherein the interfering gas is water vapor, and further comprising a step of humidifying or moistening the measuring gas, the zero gas, and the test gas.

7. A device for measuring a concentration of a detector gas in a measuring gas containing an interfering gas, comprising:

means for supplying at least one of a zero gas that is free of the detector gas and a test gas having a known concentration of the detector gas to an analyzer; and means for adding interfering gas to the measuring gas and to the zero gas to an extent such that a concentration of interfering gas in the measuring gas is equal to a concentration of interfering gas in the zero gas.

8. The device according to claim 7, further comprising a humidifier through which the measuring gas and the zero gas are directed.

9. The device according to claim 8, wherein the humidifier contains a moistening chamber through which the measuring gas and zero gas are directed and which has a moistening wall made of a material, which absorbs water and releases it to gases that are not saturated with water vapor.

10. The device according to claim 9, wherein on the side facing away from the moistening chamber, the moistening wall is in contact with water.

11. The device according to claim 9, wherein the moistening wall consists of glass-fiber-reinforced polyamide.

12. The device according to claim 9, wherein the humidifier has a water-supply chamber which is separated from the moistening chamber by the moistening wall.

13. The device according to claim 12, wherein the water-supply chamber is situated above the moistening chamber, and the moistening wall lies in a horizontal plane.

14. The device according to claim 9, wherein the moistening wall has an enlarged surface area which is greater than a surface area of a plane encompassing the enlarged surface area of the moistening wall.

15. The device according to claim 14, wherein the moistening wall has one of a meander shape and a rough surface.

16. The device according to claim 9, wherein water supplied to the moistening wall is condensate water from the measuring gas.

17. The device according to claim 7, wherein said means for adding adds interfering gas to the test gas.

18. The device according to claim 17, further comprising a humidifier through which the measuring gas, the zero gas and the test gas are directed.

19. The device according to claim 7, further comprising:

means for partially removing interfering gas from the measuring gas; and means for adding interfering gas to the partially removed measuring gas.

20. The device according to claim 18, wherein the humidifier contains a moistening chamber through which the measuring gas, test gas and zero gas are directed, and which has a moistening wall made of a material which absorbs the water and releases it to gases that are not saturated with water vapor.

21. The device according to claim 20, wherein on the side facing away from the moistening chamber, the moistening wall is in contact with water.

22. The device according to claim 20, wherein the moistening wall consists of glass-fiber-reinforced polyamide.

23. The device according to claim 20, wherein the humidifier has a water-supply chamber which is separated from the moistening chamber by the moistening wall.

24. The device according to claim 23, wherein the water-supply chamber is situated above the moistening chamber, and the moistening wall lies in a horizontal plane.

25. The device according to claim 20, wherein the moistening wall has an enlarged surface area which is greater than a surface area of a plane encompassing the enlarged surface of the moistening wall.

26. The device according to claim 25, wherein the moistening wall has one of a meander shape and a rough surface.

27. The device according to claim 20, wherein the water supplied to the moistening wall is condensate water from the measuring gas.

\* \* \* \* \*